(12) United States Patent
Eggert et al.

(10) Patent No.: US 8,940,516 B2
(45) Date of Patent: Jan. 27, 2015

(54) METHOD FOR THE SYNTHESIS OF CHIRAL CYANOHYDRINS VIA A HYDROXYNITRILE LYASE FROM BRASSICACEAE

(71) Applicant: Evocatal GmbH, Duesseldorf, DE (US)

(72) Inventors: Thorsten Eggert, Essen (DE); Jennifer Andexer, Cambridge (GB)

(73) Assignee: Evocatal GmbH, Monheim Am Rhein (DE)

( * ) Notice: Subject to any disclaimer, the term of this patent is extended or adjusted under 35 U.S.C. 154(b) by 0 days.

(21) Appl. No.: 13/680,660

(22) Filed: Nov. 19, 2012

(65) Prior Publication Data

US 2013/0149752 A1    Jun. 13, 2013

Related U.S. Application Data

(62) Division of application No. 12/517,978, filed as application No. PCT/DE2007/002216 on Dec. 10, 2007, now abandoned.

(30) Foreign Application Priority Data

Dec. 8, 2006   (DE) .......................... 10 2006 058 373

(51) Int. Cl.
   *C12P 13/00*   (2006.01)
   *C12P 7/26*    (2006.01)
   *C12N 9/88*    (2006.01)
   *C12P 21/00*   (2006.01)

(52) U.S. Cl.
   CPC ................ *C12N 9/88* (2013.01); *C12P 13/004* (2013.01)
   USPC ........... 435/232; 435/128; 435/148; 435/69.1

(58) Field of Classification Search
   USPC .................. 435/232, 148, 69.1, 128; 530/350
   See application file for complete search history.

(56) References Cited

U.S. PATENT DOCUMENTS

2005/0034196 A1   2/2005  Klessig et al.
2006/0105434 A1   5/2006  Skranc et al.

FOREIGN PATENT DOCUMENTS

| DE | 102 55 597 A1 | 6/2004 |
| DE | 102 51 547 A1 | 6/2009 |
| EP | 1026256 A2 | 8/2000 |
| WO | 03/016551 A2 | 2/2003 |
| WO | 2004/083424 A1 | 9/2004 |
| WO | 2004/090124 A2 | 10/2004 |

OTHER PUBLICATIONS

Witkowski et al., Biochemistry 38:11643-11650, 1999.*
EU *Arabidopsis* Sequencing Project, GenBank accession No. CAB96686, Nov. 2006.*
Waspi et al., Eur. J. Biochem. 254:32-37, 1998.*
Reiter et al. Applied Microbiology and Biotechnology 54:778-785, 2000.*
Ekman et al., Environ Sci Technol 39:6313-6320, 2005.*
Branden et al., Introduction to Protein Structure, Chapter 16: Prediction, Engineering, and Design of Protein Structures, Garland Publishing Inc., New York, p. 247, 1991.
Seffernick et al., "Melamine Deaminase and Atrazine Chlorohydrolase: 98 Identical but Functionally Different," J. Bacteriol. 183(8):2405-2410, Apr. 2001.
Yamada et al., "Putative alpha-hydroynitrile lyase [*Arabidopsis thaliana*]," Genbank accession No. AAK76689, Jul. 2001.
Shinn et al., "AT5g10300/F18D22_70 [*Arabidopsis thaliana*]," GenBank accession No. AAM10338, Apr. 2002.
Database EMBL [Online]: "*Arabidopsis thaliana* putative alpha-hydroxynitrile lyase (At5gl0300) mRNA, complete cds." retrieved from EBI accession No. EMBL:AY142490, Database accession No. AY142490, Sep. 24, 2002.
Weis Roland et al: "Carving the active Site of almond R-HNL for increased enanti oselectivity" in Angewandte Chemie. International Edition, Wiley VCH Verlag, Weinheim, vol. 44, No. 30, Jul. 25, 2005, pp. 4700-4704.
Fechter Martin H. et al: "Hydroxynitrile lyases: Biological sources and application as biocatalysts" in Food Technology and Biotechnology, vol. 42, No. 4, Oct. 2004, pp. 287-294.
Andexer Jennifer et al: "An R-selective hydroxynitrile lyase from *Arabidopsis thaliana* with an alpha/beta-hydrolase fold." in Angewandte Chemie (International Ed. in English) 2007, vol. 46, No. 45, Nov. 19, 2007, pp. 8679-8681.
Database: Cheuk et al., "*Arabidopsis* cDNA Clones," submitted Aug. 23, 2001 by Salk Institute Genomic Analysis Laboratory, Database accession No. AY058115, published Nov. 4, 2001.
Database: EU *Arabiodopsis* Sequencing Project, "Direct Submission," submitted Jul. 5, 2000 by MIPS, Database accession No. CAB96686, published Nov. 14, 2006.
Database: Yamada et al., "*Arabiodopsis* Full Length cDNA Clones," submitted Jul. 6, 2001 by Plant Gene Expression Center, Database accession No. AY046015, published Sep. 18, 2002.

* cited by examiner

*Primary Examiner* — Delia Ramirez
(74) *Attorney, Agent, or Firm* — Joyce von Natzmer; Agris & von Natzmer LLP

(57) ABSTRACT

The invention concerns a polypeptide which can be isolated from the Brassicaceae family and which has at least the activity of a hydroxynitrile lyase (HNL). The hydroxynitrile lyase of the invention is the first HNL from the Brassicaceae family. The plants (*Arabidopsis*) from which this enzyme or its gene is isolated is also described as non-cyanogenic. All HNL-containing plants described so far are cyanogenic plants and so it has until now been assumed that only cyanogenic plants contain hydroxynitrile lyases. Surprisingly, it transpires that a polypeptide (AtHNL) of the invention is (R)-selective. The amino acid sequence gives a theoretical molecular weight of 29.2 kDa for the AtHNL subunit. The calculated molecular mass of the protein of approximately 30 kDa can be confirmed by SDS gel electrophoresis.

14 Claims, 7 Drawing Sheets

SEQUENCE LISTING

```
<160> NUMBER OF SEQ ID NOS: 4

<210> SEQ ID NO 1
<211> LENGTH: 258
<212> TYPE: PRT
<213> ORGANISM: Arabidopsis thaliana

<400> SEQUENCE: 1
```

Met Glu Arg Lys His His Phe Val Leu Val His Asn Ala Tyr His Gly
1               5                   10                  15

Ala Trp Ile Trp Tyr Lys Leu Lys Pro Leu Leu Glu Ser Ala Gly His
                20                  25                  30

Arg Val Thr Ala Val Glu Leu Ala Ala Ser Gly Ile Asp Pro Arg Pro
            35                  40                  45

Ile Gln Ala Val Glu Thr Val Asp Glu Tyr Ser Lys Pro Leu Ile Glu
        50                  55                  60

Thr Leu Lys Ser Leu Pro Glu Asn Glu Glu Val Ile Leu Val Gly Phe
65                  70                  75                  80

Ser Phe Gly Gly Ile Asn Ile Ala Leu Ala Ala Asp Ile Phe Pro Ala
                85                  90                  95

Lys Ile Lys Val Leu Val Phe Leu Asn Ala Phe Leu Pro Asp Thr Thr
                100                 105                 110

His Val Pro Ser His Val Leu Asp Lys Tyr Met Glu Met Pro Gly Gly
            115                 120                 125

Leu Gly Asp Cys Glu Phe Ser Ser His Glu Thr Arg Asn Gly Thr Met
        130                 135                 140

Ser Leu Leu Lys Met Gly Pro Lys Phe Met Lys Ala Arg Leu Tyr Gln
145                 150                 155                 160

Asn Cys Pro Ile Glu Asp Tyr Glu Leu Ala Lys Met Leu His Arg Gln
                165                 170                 175

Gly Ser Phe Phe Thr Glu Asp Leu Ser Lys Lys Glu Lys Phe Ser Glu
            180                 185                 190

Glu Gly Tyr Gly Ser Val Gln Arg Val Tyr Val Met Ser Ser Glu Asp
        195                 200                 205

Lys Ala Ile Pro Cys Asp Phe Ile Arg Trp Met Ile Asp Asn Phe Asn
    210                 215                 220

Val Ser Lys Val Tyr Glu Ile Asp Gly Gly Asp His Met Val Met Leu
225                 230                 235                 240

Ser Lys Pro Gln Lys Leu Phe Asp Ser Leu Ser Ala Ile Ala Thr Asp
                245                 250                 255

Tyr Met

```
<210> SEQ ID NO 2
<211> LENGTH: 808
<212> TYPE: DNA
<213> ORGANISM: Arabidopsis thaliana

<400> SEQUENCE: 2
atggagagga aacatcactt cgtgttagtt cacaacgctt atcatggagc ctggatctgg      60
tacaagctca agcccctcct tgaatcagcc ggccaccgcg ttactgctgt cgaactcgcc     120
```

```
gcctccggga tcgacccacg accaatccag gccgttgaaa ccgtcgacga atactccaaa    180
ccgttgatcg aaaccctcaa atctcttcca gagaacgaag aggtaattct ggttggattc    240
agcttcggag gcatcaacat cgctctcgcc gccgacatat ttccggcgaa gattaaggtt    300
cttgtgttcc tcaacgcctt cttgcccgac acaacccacg tgccttctca cgttctggac    360
aagtatatgg agatgcctgg aggtttggga gattgtgagt tttcatctca tgaaacaaga    420
aatgggacga tgagtttatt gaagatggga ccaaaattca tgaaggcacg tctttaccaa    480
aattgtccca tagaggatta cgagctggca aaaatgttgc ataggcaagg gtcattttc    540 acagaggatc tatcaaagaa agaaaagttt agcgaggaag gatatggttc ggtgcaacga    600
gtttacgtaa tgagtagtga agacaaagcc atccctgcg atttcattcg ttggatgatt    660
gataatttca acgtctcgaa agtctacgag atcgatggcg gagatcacat ggtgatgctc    720
tccaaacccc aaaaactctt tgactctctc tctgctattg ccaccgatta tatgtaataa    780
tcttaagtcc gttttacttt tttctcat                                      808

<210> SEQ ID NO 3
<211> LENGTH: 40
<212> TYPE: DNA
<213> ORGANISM: Artificial Sequence
<220> FEATURE:
<223> OTHER INFORMATION: 5' primer

<400> SEQUENCE: 3
tataccatgg agaggaaaca tcacttcgtg ttagttcaca                          40

<210> SEQ ID NO 4
<211> LENGTH: 40
<212> TYPE: DNA
<213> ORGANISM: Artificial Sequence
<220> FEATURE:
<223> OTHER INFORMATION: 3' primer

<400> SEQUENCE: 4
tatactcgag ttacatataa tcggtggcaa tagcagagag                          40
```

METHOD FOR THE SYNTHESIS OF CHIRAL CYANOHYDRINS VIA A HYDROXYNITRILE LYASE FROM BRASSICACEAE

CROSS-REFERENCE TO RELATED APPLICATIONS

This is a divisional application claiming the benefit of U.S. application Ser. No. 12/517,978 filed Dec. 11, 2009, now abandoned, which is the U.S. national stage of International application no. PCT/DE2007/02216, filed Dec. 10, 2007 designating the United States and claiming priority to German application no. DE 10 2006 058 373.6, filed Dec. 8, 2006.

FIELD OF THE INVENTION

The invention relates to a polypeptide isolated from plants from the Brassicaceae family. The invention also relates to polypeptides which exhibit hydroxynitrile lyase activity. Further, the invention relates to the use of these polypeptides and to methods wherein the polypeptide is used as a catalyst. Furthermore, the invention relates to nucleic acids which code for the polypeptides of the invention.

BACKGROUND OF THE INVENTION

Hydroxynitrile lyases (HNLs) (EC 4.1.2.10, EC 4.1.2.11, EC 4.1.2.37, EC 4.1.2.39) catalyze the enantioselective cleavage of cyanohydrins to a carbonyl compound (aldehyde or ketone) and hydrocyanic acid.

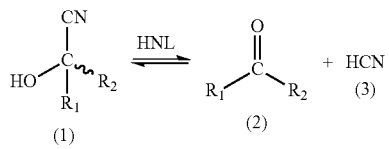

Reaction Catalyzed by HNL:

In the natural reaction a cyanohydrin (1) is cleaved into a carbonyl compound (aldehyde or ketone) (2) and hydrocyanic acid (3), while a chiral cyanohydrin is produced from the latter ones in industrial approaches.

HNL activity was initially detected in 1908 by Rosenthaler in emulsin from almonds. Representatives of this class of enzyme are primarily found in plants, and occasionally also in insects and bacteria. All known HNLs have been isolated from plants; in nature, the catalyzed reaction serves to ward off aggressors which would feed on them. This release of hydrocyanic acid from cyanohydrins is also termed cyanogenesis. The reverse reaction, i.e. the formation of a chiral cyanohydrin from an aldehyde or a ketone and hydrocyanic acid, which is also catalyzed by HNLs, is used industrially. Chiral cyanohydrins constitute important precursors in the manufacture of β-aminoalcohols and α-hydroxy acids, for example.

The per se highly heterogeneous class of enzymes can be roughly divided into two groups which differ in the presence of the cofactor FAD. The essential FAD molecule appears, however, to have an exclusively structural function; a biochemical significance for the catalyzed reaction has not yet been reported. FAD-containing HNLs have until now only been described for the Rosaceae family—examples of the extensively biochemically characterized representatives are the enzymes from *Prunus amygdalus* (PaHNL, almond) and *Prunus mume* (PmHNL, Japanese apricot). The sequences of the enzymes are very similar and all exhibit (R)-selectivity in the formation of chiral cyanohydrins.

The group of non-cofactor-containing HNLs is much more heterogeneous. Examples which can be mentioned are the enzyme from *Linum usitatissimum* (LuHNL, linseed, (R)-selective) and *Sorghum bicolor* (SbHNL, millet, (S)-selective). Further, the group includes enzymes from *Hevea brasiliensis* (HbHNL, rubber tree) and *Manihot esculenta* (MeHNL, cassava). Although the HNL from linseed has similarities with zinc-dependent alcohol dehydrogenases and that from millet has similarities to carboxypeptidases, the latter enzymes (as well as carboxypeptidases) belong to the α/β hydrolase group and are exclusively (S)-selective. In addition to the common fold motif (see below), the two proteins are also sequentially very similar (77% identity for the amino acids).

In addition to the cited HNLs from cassava and the rubber tree, various enzyme groups such as lipases, esterases, proteases, epoxyhydrolases and dehalogenases belong to the α/β-hydrolase family. All in all, the fold motif consists of mainly parallel β-leaflet strands which are surrounded by α-helices. The active centre is formed by three residues, the so-called catalytic triad (Ollis et al., 1992). The structures of the two HNLs with a α/β hydrolase fold motif (HbHNL, MeHNL) have been resolved and the catalytic residues have been unambiguously identified.

Further differences in the various HNLs concern their substrate spectra and enantioselectivities. The articles by Fechter et al (2004) and Sharma et al (2005) provide an overview of the known enzymes.

Enzymes which are of application on an industrial scale should have a broad substrate spectrum and high enantioselectivity. Furthermore, it is advantageous if the appropriate enzyme can be manufactured in a recombinant manner. An overview of the most important HNLs and their properties is given in Table 1.

TABLE 1

Overview of properties of the most industrially important HNLs.

| Original organism | Stereo-selectivity | Recombinant expression host | Substrate Aldehyde Aliphatic | Aromatic | Ketone Aliphatic | Aromatic | Misc | Literature |
|---|---|---|---|---|---|---|---|---|
| *Manihot esculenta* or MeHNL-"tunnel mutation" W128A | S | E. coli | + | + | + | + Methyl ketone | | Buhler et al., 2003 |
| *Hevea brasiliensis* | S | E. coli P. pastoris S. cerevisiae | + | + | + | + Methyl ketone | | Hasslacher et al., 1997 U.S. Pat. No. 6,337,196 B1 |

TABLE 1-continued

Overview of properties of the most industrially important HNLs.

| Original organism | Stereo-selectivity | Recombinant expression host | Substrate | | | | Misc | Literature |
|---|---|---|---|---|---|---|---|---|
| | | | Aldehyde | | Ketone | | | |
| | | | Aliphatic | Aromatic | Aliphatic | Aromatic | | |
| Prunus amygdalus (isoenzyme 5) | R | P. pastoris | + | + | + | + | Glycosylated FAD cofactor | Glieder et al., 2003 EP 1223220 B1 |
| Linum usitatissimum | R | E. coli P. pastoris | + | − | + | − | | Albrecht et al., 1993 |

Chiral cyanohydrins can be produced with the aid of HNLs in both aqueous systems and in organic solvents such as diisopropylether (DIPE). Frequently, two-phase systems such as DIPE/buffer can be used. The advantage in using organic solvents, in addition to the good solubility of the substrates and products, lies in the suppression of the non-catalyzed chemical reaction of aldehyde/ketone and hydrocyanic acid to racemic cyanohydrin. Since this unwanted reaction is temperature-dependent and only occurs at pHs of more than 5, it can also be prevented by dropping the pH to below 5 and a relatively low reaction temperature (<10° C.). Very recently, moreover, there have been reports of initial tests using HNLs in ionic liquids (Gaisberger et al, 2004). The HNLs in question are used in various preparations: as the dissolved enzyme, lyophilisate, immobilisate on various carrier materials, CLECs (cross-linked enzyme crystals) or CLEAS (cross-linked enzyme aggregates).

U.S. Pat. No. 6,337,196 B1, for example, describes the production of (S)-cyanohydrins with the HNL from *Hevea brasiliensis*. DE 100 62 306 A1 describes the production of (R)-cyanohydrins with the HNL from *Prunus amygdalus*. Other specific examples for the use of (R) and (S) cyanohydrins can be found in the articles by Schmidt et al (1999) and Fechter et al (2004).

(S)-selective enzymes, which are currently used industrially, are HNLs from *Hevea brasiliensis* (HbHNL) and *Manihot esculenta* (MeHNL); both can readily be produced in microbial hosts and cover a broad substrate spectrum (aliphatic and aromatic aldehydes and ketones, preferably methylketone). The equally (S)-selective enzyme from *Sorghum bicolor* has until now not been used as it cannot be produced in heterologous hosts.

EP 1 223 220 A1 describes the use of the (R)-selective HNL from *Prunus amygdalus* (PaHNL, isoenzyme 5). The enzyme can be produced heterologously, but until now only expression in a eukaryotic host (*Picha pastoris*) has been successful. The equally (R)-selective HNL from linseed (LuHNL) can be expressed heterologously in bacteria, but suffers from the drawback that only aliphatic substrates are accepted and so use on an industrial scale is correspondingly limited.

Thus, there is considerable interest in discovering further (R)-selective HNLs with new enzymatic properties, which in particular are suitable for the transformation of aromatic and aliphatic aldehydes and ketones and in addition can be expressed in good yields in bacterial hosts.

BRIEF DESCRIPTION OF THE INVENTION

Hence, it is the object of the invention to produce novel HNLs which are readily accessible and which can be used in an organic synthesis for the synthesis of chiral (R)-cyanohydrins.

This object is achieved in accordance with the invention by providing a polypeptide which can be isolated from plants from the Brassicaceae family and which exhibits at least the activity of a hydroxynitrile lyase.

The hydroxynitrile lyase of the invention is the first HNL from the Brassicaceae family. The plant from which this enzyme or gene is isolated is also described as being non-cyanogenic. All HNL-containing plants described until now are cyanogenic plants, and until now it has been assumed that only cyanogenic plants contain hydroxynitrile lyases. In *Arabidopsis*, until now neither cyanogenic glycosides (stable storage form of cyanohydrin) nor cyanohydrins have been detected. The presence of the catabolic enzyme was thus explicitly excluded (Wäspi et al, 1998). Although the natural function of the enzyme in *Arabidopsis* is currently unknown, the novel enzyme is a very interesting alternative to the HNLs used until now for enzymatic production. Surprisingly, it has transpired that the polypeptide of the invention is (R)-selective. Because of the homology to enzymes from cassava and the rubber tree, which both exhibit characteristic α/β-hydrolase folding, (S)-selectivity was expected, since until now all HNLs which exhibit said fold motif are (S)-selective.

A specific object of the invention was also grounded in the capability of the HNL of accepting carbonyl compounds with aromatic side chains. An example of such a sterically challenging substrate which may be cited is benzaldehyde, which produces mandelonitrile. The broad substrate spectrum of the polypeptide of the invention, which encompasses both aliphatic and aromatic compounds, and the process stability which is suitable for industrial applicable means that many applications are possible. A further advantage lies in the fact that the polypeptide of the invention can be produced cheaply and effectively in *E. coli*.

Preferably, the polypeptide of the invention comprises at least one amino acid sequence in accordance with SEQ ID NO: 1. Surprisingly, it has been shown that the polypeptide of the invention which can be expressed from *Arabidopsis thaliana* (AtHNL) has enzymatic hydroxynitrile lyase activity although *A. thaliana* is not a cyanogenic plant (Wäspi et al, 1998). In particular, the AtHNL of SEQ ID NO: 1 transforms carbonyl compounds with aromatic or aliphatic side chains. Further, the hydroxynitrile lyase of the invention stands out because of its excellent stereoselectivity. Thus, even sterically challenging substrates are transformed into the desired corresponding optically active cyanohydrins with high enantioselectivities of >95% ee.

Thus, a preferred embodiment of the invention, the polypeptide or hydroxynitrile lyase (AtHNL) from *Arabidopsis thaliana*, has the following amino acid sequence (SEQ ID NO: 1):

```
merkhhfvlv hnayhgawiw yklkpllesa ghrvtavela asgidprpiq avetvdeysk plietlkslp eneevilvgf sfgginiala adifpakikv lvflnaflpd tthvpshvld kymempgglg dcefsshetr ngtmsllkmg pkfmkarlyq ncpiedyela kmlhrqgsff tedlskkekf seegygsvqr vyvmssedka ipcdfirwmi dnfnvskvye idggdhmvml skpqklfdsl saiatdym
``` or an allele or functional variant thereof, or a functional partial sequence thereof.

Particularly, preferably, the polypeptide differs from the polypeptide of SEQ ID NO: 1 in one or more amino acid replacement(s). Particularly advantageously, the asparagine in position 12 has been exchanged for threonine (N12T) or alanine (N12A), preferably in combination with an exchange of tyrosine in position 14 for cysteine (Y14C) or alanine (Y14A). By dint of this exchange of the amino acids in position 12, possibly in combination with the exchange in position 14, the substrate spectrum of the polypeptide of the invention can advantageously be extended to better encompass the acceptance of ketones. Further, an exchange of leucine in position 129 for tryptophan (L129W) and/or the exchange of tyrosine in position 14 for cysteine (Y14C) reverses the enantioselectivity, i.e. from (R) selectivity to (S)-selectivity.

The term "functional variants" as used in the context of this invention means a polypeptide or protein containing an amino acid sequence with a sequence homology of more than 85%, preferably more than 90%, particularly preferably more than 95%. Moreover, the term "functional partial sequence" also means polypeptides or proteins which contain amino acid fragments of at least 50 amino acids, preferably at least 100 amino acids, particularly preferably more than 150 amino acids, as well as functional variants with deletions of up to 100 amino acids, preferably up to 50 amino acids, particularly preferably up to 20 amino acids, in particular up to 10 amino acids, fall within the definition of "functional partial sequence". Thus, the invention also encompasses polypeptides which differ from the polypeptides of the invention by a deletion, insertion and/or substitution of at least one and at most 100 amino acids, preferably 1 to 50 amino acids, particularly preferably 1 to 20 amino acids and more particularly 1 to 10 amino acids.

The hydroxynitrile lyase of the invention can also have post-translational modifications, such as glycosylations or phosphorylations.

Further, the invention encompasses proteins, in particular fusion proteins, which comprise at least one polypeptide of the invention.

The present invention also relates to nucleic acids coding for the polypeptides or proteins or hydroxynitrile lyases or an allelic or functional variant thereof or a partial sequence or DNA fragment thereof, which are complementary to such nucleic acid sequences which hybridize with coding nucleic acids under stringent conditions.

In particular, the invention encompasses isolated and/or recombinant nucleic acid molecules which comprise at least one nucleotide sequence for the synthesis of at least one polypeptide, wherein the nucleotide sequence is selected from the group consisting of:

a) a nucleotide sequence which codes for a polypeptide of the invention from the Brassicaceae family;

b) a nucleotide sequence which codes for a polypeptide which comprises at least the amino acid sequence of SEQ ID NO: 1;

c) a nucleotide sequence which comprises the sequence of SEQ ID NO: 2;

d) a nucleotide sequence which codes for fragments of the polypeptide coded by the nucleotide sequences of a), b) or c), wherein the fragments have the catalytic activity of the polypeptides coded by the nucleotide sequences of a), b) or c);

e) a nucleotide sequence which differs from the nucleotide sequences of a), b), c) or d) by replacement of at least one codon for a synonymous codon;

f) a nucleotide sequence, the complementary strand of which hybridizes with the nucleotide sequences of a), b), c) or d) and which codes for at least one polypeptide which has the catalytic activity of the polypeptide coded by the nucleotide sequences of a), b), c) or d);

g) a nucleotide sequence which has at least 85%, preferably 90%, in particular 95% identity with the nucleotide sequence of a), b), c) or d) and which codes for at least the polypeptide which has the catalytic activity of the polypeptide coded by the nucleotide sequences of a), b), c) or d);

h) a nucleotide sequence which corresponds to the complementary strand of the nucleotide sequence of a) to g).

As an example, the hydroxynitrile lyase gene from *Arabidopsis thaliana* contains the following nucleic acid coding (SEQ ID NO: 2):

```
ATGGAGAGGAAACATCACTTCGTGTTAGTTCACAACGCTTATCATGGAGCCTGGATCTGG

TACAAGCTCAAGCCCCTCCTTGAATCAGCCGGCCACCGCGTTACTGCTGTCGAACTCGCC

GCCTCCGGGATCGACCCACGACCAATCCAGGCCGTTGAAACCGTCGACGAATACTCCAAA

CCGTTGATCGAAACCCTCAAATCTCTTCCAGAGAACGAAGAGGTAATTCTGGTTGGATTC

AGCTTCGGAGGCATCAACATCGCTCTCGCCGCCGACATATTTCCGGCGAAGATTAAGGTT

CTTGTGTTCCTCAACGCCTTCTTGCCCGACACAACCCACGTGCCTTCTCACGTTCTGGAC

AAGTATATGGAGATGCCTGGAGGTTTGGGAGATTGTGAGTTTTCATCTCATGAAACAAGA
```

-continued

```
AATGGGACGATGAGTTTATTGAAGATGGGACCAAAATTCATGAAGGCACGTCTTTACCAA

AATTGTCCCATAGAGGATTACGAGCTGGCAAAAATGTTGCATAGGCAAGGGTCATTTTTC

ACAGAGGATCTATCAAAGAAAGAAAAGTTTAGCGAGGAAGGATATGGTTCGGTGCAACGA

GTTTACGTAATGAGTAGTGAAGACAAAGCCATCCCCTGCGATTTCATTCGTTGGATGATT

GATAATTTCAACGTCTCGAAAGTCTACGAGATCGATGGCGGAGATCACATGGTGATGCTC

TCCAAACCCCAAAAACTCTTTGACTCTCTCTCTGCTATTGCCACCGATTATATGTAATAA

TCTTAAGTCCGTTTTACTTTTTTCTCAT
```

SEQ ID NO: 2 and its allelic or functional variants with a homology of more than 50%, preferably more than 75%, particularly preferably more than 90% and most preferably more than 95% or the partial sequence thereof consisting of at least 150 nucleotides, preferably at least 300 nucleotides, particularly preferably at least 500 nucleotides, or DNA fragments which are complementary to such nucleic acid sequences which hybridize with a coding nucleic acid sequence SEQ ID NO: 2 or an allelic or functional variation or partial sequence thereof under stringent conditions, belong to the preferred nucleic acids of the invention. In this manner, routine hybridization conditions can be used.

The information from SEQ ID NO: 2 can be used to produce primers for the identification and cloning of directly homologous forms using PCR. Moreover, because of the sequence information, probes to investigate further naturally occurring functional variants of the athnl gene and thus the corresponding coding enzyme variants can be used. Starting from SEQ ID NO: 2 or from allelic or naturally occurring functional variants thereof, e.g. via PCR using a deficient DNA polymerase, a bank of artificially produced functional enzyme variants can be produced. Similarly, standard methods can be used to introduce individual point mutations into the DNA sequence which lead to amino acid exchanges; this means that the protein's properties such as substrate specificity can be changed.

The following point mutations are particularly preferred in the nucleotide sequence of SEQ ID NO: 2, either individually or in any combination:
a) exchange of $2^{nd}$ nucleotide (A=adenine) of the $12^{th}$ codon (AAC) for cytosine (C), i.e. transformation into the codon with the nucleotide sequence ACC or alternatively exchange of the whole $12^{th}$ codon for the codon ACT, ACA or ACG or GCT, GCC, GCA or GCG;
b) exchange of $2^{nd}$ nucleotide (A=adenine) of the $14^{th}$ codon (TAT) for guanine (G), i.e. transformation into the codon with the nucleotide sequence TGT or alternatively exchange of the whole $14^{th}$ codon for the codon TGC or GCT, GCC, GCA or GCG;
c) exchange of $2^{nd}$ nucleotide (T=thymine) of the $129^{th}$ codon (TTG) for guanine (G), i.e. transformation into the codon with the nucleotide sequence TGG;

The coding DNA sequences can be cloned into routine vectors and, after transforming host cells with said vectors, can be expressed in cell culture. Examples of suitable expression vectors are pET-28a(+) for E. coli, and also expression vectors of other prokaryotic single cell organisms can be used. Examples of suitable expression vectors for yeasts are the pREP vector or pINT vector. For expression in insect cells, baculovirus vectors are suitable, such as those disclosed in EP-B1-0 127 839 or EP-B1-0 549 721, and for expression in mammalian cells, SV40 vectors, for example, are suitable; they are readily obtainable.

In addition to the usual markers, such as kanamycin resistance, the vectors may contain other functional nucleotide sequences for regulation, in particular repression or induction of the expression of the HNL gene and/or the reporter gene. Preferably, the promoters are inducible promoters, such as the rha-promoter or the nmtl-promoter, or strong promoters such as the lac-, ara-, lambda-, pL-, T7- or T3-promoter. The coding DNA fragments must be transcribable in the vectors from one promoter. Examples of further reliable promoters are the baculovirus-polyhedrin promoter for expression in insect cells (see, for example, EP-B1-0 127 839) or the early SV40 promoter or the LTR promoters, for example from MMTV (mouse mammary tumour virus, Lee et al, 1981).

The expression vectors of the invention may contain further functional sequence regions, such as a replication start point, operators, termination signals, tags which facilitate purification (for example a His-tag, a Strep-tag) or other peptide sequences which are produced by the fusion proteins.

With the vectors described, host cells can be transformed using the usual methods, such as the heat shock method or by electroporation.

Thus, in a further aspect, the present invention is constituted by expression systems which comprise host cells or host cell cultures which are transformed with the vector systems just described. Preferred hosts are single-cell prokaryotic organisms, in particular E. coli. In the case of the expression of eukaryotic hnl genes of the invention, it may be advantageous to use eukaryotic expression systems in order, for example, to introduce post-translational modifications which are typical of eukaryotes into the hnl gene product. Particularly suitable eukaryotic host cells are yeasts.

A preferred expression system contains a hydroxynitrile lyase gene in accordance with SEQ ID NO: 2 or an allelic or functional variation or a partial sequence thereof in a vector which is suitable for expression in E. coli, such as a pET-28a (+) vector wherein the hydroxynitrile lyase gene must be transcribably cloned into the vector. Preferably, the introduced hnl gene is cloned into the pET-28a(+) vector such that the transcription is under the control of the IPTG-inducible promoter present in the vector. Alternatively, rhamnose-inducible promoters may be used.

The expression systems can be cultivated using standard protocols which are known to the skilled person. Depending on the transcription control and the vector employed, expression of the gene introduced into the expression system can be regulated either constitutively or, as for example when pET-28a(+) is used as the expression plasmid, with added IPTG. After expression of a hydroxynitrile lyase of the invention, it is purified, for example using chromatography or by centrifuging. In order to carry out catalytic reactions, the purified enzymes and also the raw extracts or centrifugation residues or fractions can be used directly. The enzymes can be used both as a catalyst, lyophilisate or immobilisate dissolved in aqueous buffer on various carrier materials (both covalent and non-covalent binding as well as CLEAs or CLECs).

Thus, the invention also pertains to cells or cell cultures which comprise at least one nucleic acid molecule of the invention or at least one vector containing it.

The invention also encompasses the use of the polypeptide of the invention, or the protein of the invention, or the cells of the invention, or the cell culture of the invention, for the production of chiral cyanohydrins. Thus, in a further aspect, the present invention concerns the use of hydroxynitrile lyases of the invention for the catalytic production of chiral cyanohydrins.

Furthermore, the invention encompasses a method for the synthesis of chiral cyanohydrins from at least one carbonyl compound and hydrocyanic acid, wherein the reaction is carried out in the presence of the polypeptide of the invention or the protein of the invention or the cells of the invention or the cell culture of the invention. The carbonyl compound may be an aliphatic or aromatic aldehyde. Alternatively, the carbonyl compound may also be an aliphatic or aromatic ketone. The carbonyl compounds may also be transformed with other nucleophiles instead of HCN.

The invention also encompasses a method for cleaving cyanohydrins into at least one carbonyl compound and hydrocyanic acid, wherein the reaction is carried out in the presence of the polypeptide of the invention, or the protein of the invention or the cells of the invention or the cell culture of the invention.

BRIEF DESCRIPTION OF THE FIGURES

The invention will now be described with reference to the accompanying figures and examples, in which.

DESCRIPTION OF EXEMPLARY AND PREFERRED EMBODIMENTS OF THE INVENTION

Figure 1:
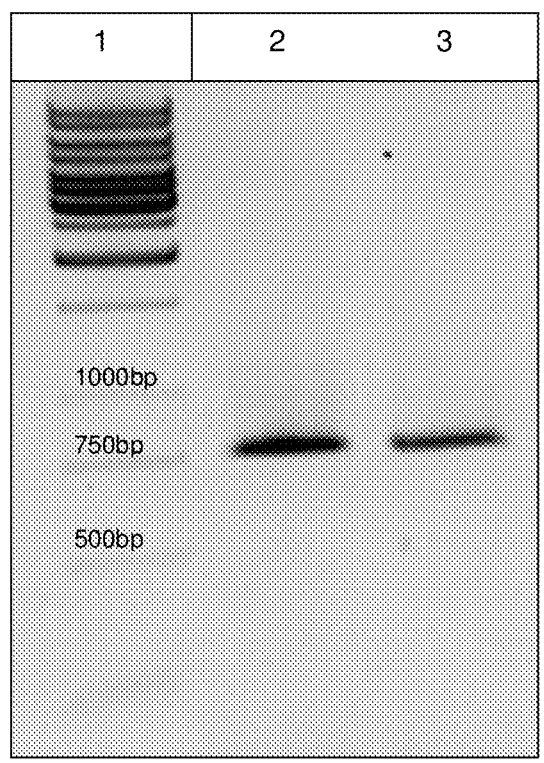
FIG. 1 is a DNA-agarose gel with PCR-products (AtHNL) from cDNA from *Arabidopsis*-germs: 1=Marker, 2 and 3=PCR-products (AtHNL, the PCR product is approximately 780 base pairs long and thus corresponds to the length of the gene in the databases)

A polypeptide of the invention from the non-cyanogenic plant *Arabidopsis thaliana* will now be described by way of example. The results given will be illustrated and substantiated using detailed examples.

A database search carried out with the amino acid sequence of MeHNL indicated that in the *Arabidopsis thaliana* plant there were many homologous proteins for which a hydroxynitrile lyase activity had, however, never been described. The *Arabidopsis thaliana* plant (mouse-ear cress) is a model organism (accessible genome, short generation period) and thus has been comprehensively investigated. The genome has been completely sequenced and recorded in sequence databases. Examples of such databases are, for example, the "Genbank" as a collection of all published sequences, or TAIR as a database restricted to a single organism (in this case *Arabidopsis*). Because of the great strides made in molecular biology, many new sequences are being input into the appropriate databases than can be individually assessed and described. Thus, until now genes which have been identified as true genes but which have not been further investigated have automatically been ascribed types by appropriate computer algorithms because of their similarities to known sequences. Whether the function stated in this description is true, however, must be individually ascertained for each protein. Some of the proteins from *Arabidopsis* ascribed as putative HNLs by homology with HNLs from cassava had already been cloned during studies, expressed heterologously in *E. coli* and tested for HNL activity (with the substrates acetocyanohydrin and mandelonitrile), but HNL activity could not be established in four out of five of the investigated proteins. Surprisingly, the fifth protein (At5g10300) had high activity as regards the cleavage of mandelonitrile (see Example 6 (Ia)).

The gene sequence of the novel HNL (hereinafter AtHNL) as described above derives from *Arabidopsis thaliana* (mouse-ear cress) and exhibits a high degree of homology with enzymes from *hevea brasiliensis* and *Manihot esculenta*. The gene (see SEQ ID NO: 1) is described as a homologous sequence in the appropriate literature regarding α/β hydrolases, but HNL activity was not assumed since *Arabidopsis thaliana* is not known as a plant which can lead to cyanogenesis (Wäspi, 1998). The gene appears in the databases under accession number NP_196592 (Genbank) or At5g10300 (TAIR-nomenclature) and is automatically ascribed as a putative hydroxynitrile lyase. This gene is not described in the literature as HNL. The description is found in addition to the cited HNL publications in investigations of the *Arabidopsis* genome or specific parts (for example water-stress regulated gene) (Bray, 2002)).

Only one out of five tested enzymes which all exhibit significant similarity with enzymes from cassava and the rubber tree, actually had the predicted activity. Consequently, in this case too no prediction regarding the activity of a protein can be made on the grounds of the sequence comparison alone. Concerning the sequence then, gene sequences of interest had to be individually cloned, expressed and tested for activity.

Example 1

Database Search

A database search was carried out with the amino acid for the HNL from Manhiot esculenta (Protein-Protein Blast, standard adjustment the results were filtered onto the organism *Arabidopsis thaliana*. The resulting list contains 22 sequences with at least 47% similarity as regards the amino acid sequence; 5 thereof are listed in Table 2. The genes listed in Table 2 were cloned, expressed and investigated for HNL activity.

TABLE 2

List of genes resembling MeHNL from *Arabidopsis thaliana*

| TAIR-nomenclature | Accession no. | Similarity to MeHNL (%) | Remarks/misc |
|---|---|---|---|
| At4g0990 | NM 117058 | 50 | Cloned and expressed, no activity |
| At3g10870 | AY096692 | 48 | Cloned and expressed, no activity |
| At3g50440 | AY142031 | 57 | Cloned and expressed, no activity |
| At4g37150 | BT006227 | 56 | Cloned and expressed, no activity |
| At5g10300 | NP 196592 | 67 | Cloned and expressed, HNL activity (a polypeptide in accordance with the invention) |

Example 2

Amplification of Gene At5g10300 (Hereinafter AtHNL) from cDNA, Cloning in Expression Vector pET28a and Transformation in *E. coli* mRNA was isolated from *Arabidopsis* germs using "RNeasy® Plant Mini Kits" from Qiagen; the procedure was carried out in accordance with the instructions contained in the kit. Using "RevertAid™ First Strand cDNA Synthesis Kits" from Fermentas, the mRNA obtained was transcribed into cDNA. This acted as the target structure for amplification of the HNL-homologous gene. PCR was carried out with sequence-specific primers (SEQ ID NO: 3 & 4) at an annealing temperature of 58° C. After purification of the PCR product on a DNA agarose gel (FIG. 1) using a commercially available gel elution kit, sticky ends were produced with the restriction enzymes NcoI and XhoI. Next, the fragment could be cloned into the vector pET28a which had also been cleaved with the same restriction enzymes. Ligation was carried out for 16 h at 16° C. The sequence of the thus cloned insert was confirmed by sequencing.

The plasmid described above (pAtNHL) can be transformed in the bacterial host *Escherichia coli* and the corresponding gene product can be expressed. To this end, (chemically or electrocompetently) competent *E. coli* BL21 (DE3) cells were transformed using standard methods with pATHNL. Successfully transformed clones could be selected on LB agar plates with the antibiotic Kanamycin.

Example 3

Expression of Plasmids in *E. coli*

Figure 2:
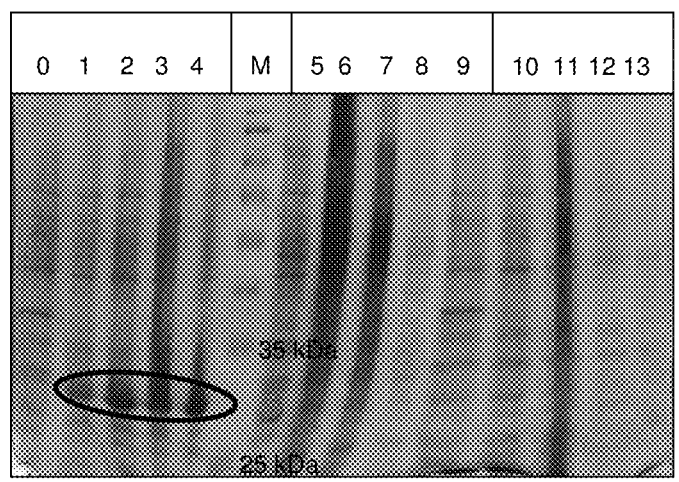
FIG. 2 is a SDS polyacrylamide gel to assay induced gene expression in *E. coli* cells which contain the plasmid pAtHNL: M=Marker, 0-4=induced, 5-9=not induced, 10-13=empty vector; to assay the expression, culture samples taken at the time of protein expression (addition of IPTG) were placed on SDS gel (0-4 h post-induction), the control was a non induced culture and the empty vector was pET28a; at the expected height of ca. 30 kDa in the induced culture is a band which increases with time (marked)—this is not present in the two controls.

For the expression of HNL, initially an overnight culture of *E. coli* (BL21(DE3), transformed with pAtHNL) at 30° C. in LB-Medium with 50 µg/mL kanamycin was inoculated with a single colony, The next morning, the main culture (also LB-medium/kanamycin) was over-inoculated with the pre-culture in a ratio of 1:20. Once an optical density of 0.6 to 0.8 had been reached at 550 nm, the cultures were induced with 0.4 mM of IPTG. After growing for 5 h at 30° C., the cells could be harvested by centrifuging and stored at −20° C. Expression success was monitored on SDS-polyacrylamide gel (FIG. 2). The amino acid sequence gave a theoretical molecular weight of 29.2 kDa for the AtHNL subunit.

Example 4

Purification of Proteins

Centrifuged cells (15-20 g, Example 3) were re-suspended in solubilizing buffer (50 mM KPi, pH 5.5) and placed on an equilibrated Q-sepharose column (bed volume approx 25 mL). AtHNL active fractions were identified by activity tests (mandelonitrile cleavage, see Example 6, Ia).

Figure 3:
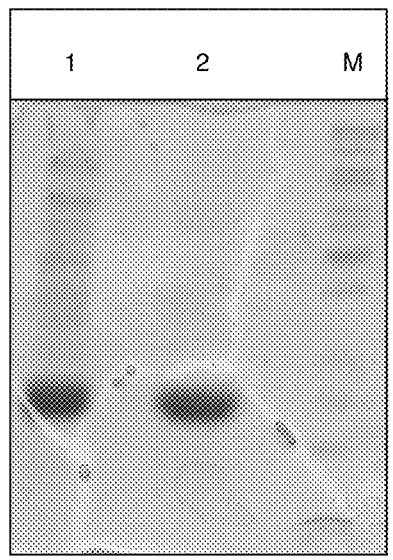
FIG. 3 is a SDS-polyacrylamide gel to confirm purification of the polypeptide of the invention (AtHNL): M=Marker, 1=after Q-Sepharose, 2=after gel filtration; solubilized unrefined cell extract is initially purified on an anion exchanger (Q-Sepharose), followed by a second purification step using gel filtration chromatography.

A portion of the protein eluted at the end of the run, the remainder at very low concentrations of salt (approx 0.15 M NaCl). The fractions which eluted over the salt gradient were desalted on a Sephadex G-25 column (1 L bed volume, buffer: 10 mM KPi, pH 6). The eluted fractions from the G-25 were purified and lyophilized. For further purification, the lyophilisate (approx 250 mg) was taken up in a little buffer (10 mM acetate, pH 6, 150 mM NaCl) and placed on a gel filtration column (Sephadex G-200, bed volume 125 mL) (FIG. 3). Next, the active fractions were either lyophilized again or concentrated in Centricons (VivaSpin (VivaScience), cut-off volume 10 kDa).

Example 5

Protein Chemical Characterization a. Molecular Mass

The calculated molecular mass of the protein of approx 30 kDa can be confirmed by SDS gel electrophoresis (see FIGS. 2 and 3).

b. Oligomeric Condition

After calibration of the Sephadex G200-column with ribonuclease A (13.7 kDa), chymotrypsinogen A (25 kDa), ovalbumin (43 kDa), albumin (67 kDa), aldolase (158 kDa), catalase (232 kda), and blue dextran 2000 (2000 kDa), the molecular weight of the native protein came out at approx 50 kDa. It was concluded that the protein was present as the dimer (monomer, calculated from sequence: 29.2 kDa).

c. Optimum pH

Figure 4:
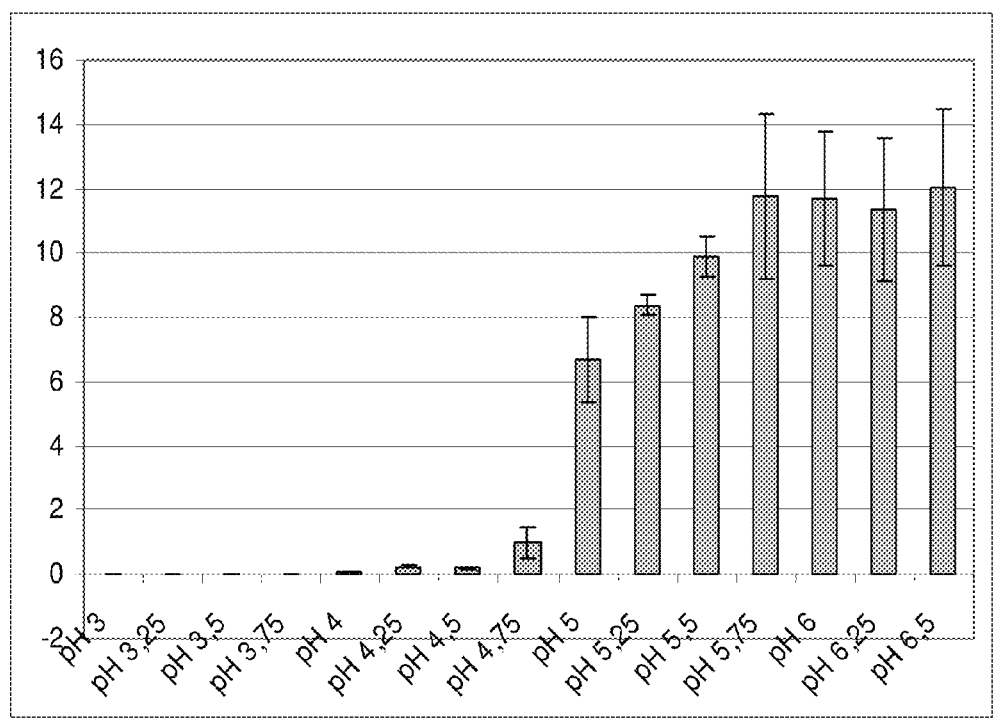
FIG. 4 is a bar chart of the enzymatic activity of the polypeptide of the invention at various pHs: the optimum pH for AtHNL is at approximately 5.75, the activity is measured from pH 4.25; from a pH of 5, the activity increases sharply.

The optimum pH was determined using the enzyme test described in Example 6 (II). A low activity can already be reproducibly measured from a pH of 4.25; at a pH of 5, the activity rises sharply. At a pH of 5.75, the maximum value is reached and this value remains the same up to the highest measured value (pH 6.5) (FIG. 4). Values over a pH of 6.5 could not be measured since the background due to self degradation of the substrate was too high.

d. Stability Under Reaction Conditions

Figure 5:
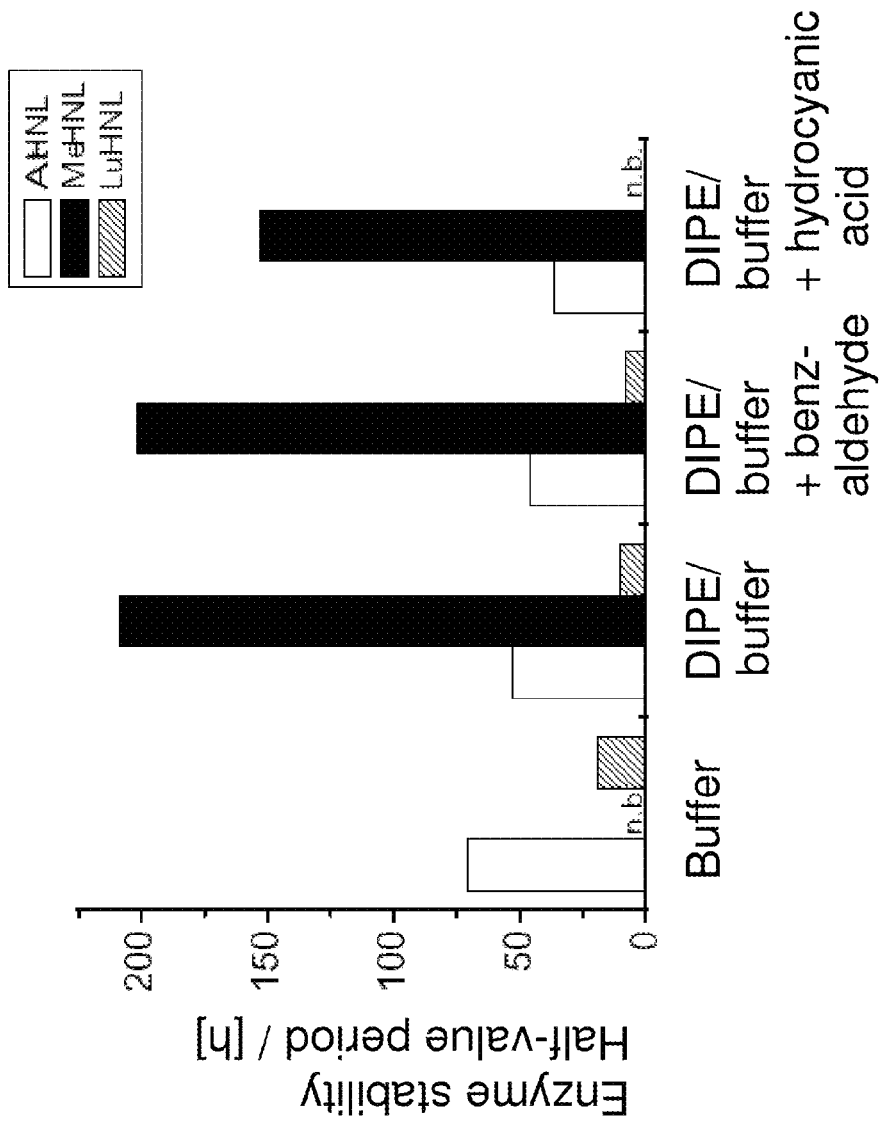
FIG. 5 is a bar chart of the stability of the polypeptide of the invention under reaction conditions compared with hydroxynitrile lyases from cassava and linseed: the half lives under the reaction conditions for the AtHNL from *Arabidopsis* are compared with the (S) selective HNL from cassava and the (R) selective HNL from linseed.

In order to be able to estimate the suitability for use in industrial applications, the protein had to be investigated as regards the stability in the reaction system used therein. An example of a reaction system which is frequently used in high-tech processes is a two-phase system of buffer and diisopropylether (1:1). The incubation conditions correspond to the conditions of the synthesis reaction given in Example 6 (II). The remaining activity after various times was determined using a slightly modified cleavage test (cf Example 6 (Ia)). The comparisons were the (S) selective HNL from *Manihot esculenta* (MeHNL) and the (R) selective HNL from *Linium usitatissimum* LuHNL. In direct comparison with the homologous protein MeHNL, the stability periods determined for AtHNL were much shorter; compared with the LuHNL enzyme, also (R) selective, the values are indeed much better (up to four times higher, FIG. 5)). All of the half lives were over the maximum times for cyanohydrin syntheses (10-24 h) which are in general use.

Example 6

Substrate Spectrum and Stereoselectivity

The HNL activity was determined both by the cleavage of cyanohydrins and also by the synthesis of cyanohydrins. To this end, various activity tests were used. For a better overview, all of the test systems used are described first, with the results being given later.

Ia) Cleavage of Mandelonitrile(=Benzaldehyde Cyanohydrin), Determination of Liberated Benzaldehyde (Cell Test):

The protocol employed was based on the test described by Bauer et al in 1999 and was only modified slightly. 700 µl of citrate-phosphate buffer, pH 5 (48.5 mL 0.1M citric acid, 51.5 mL 0.2 M dipotassium hydrogen phosphate, qsp 100 ml water) was mixed with 100 µl of enzyme sample in a quartz glass cell and the reaction was started with 200 µl of mandelonitrile solution (60 mM in citrate-phosphate buffer, pH 3.5 (1.82 mL 0.1 M citric acid, 1.06 mL 0.1 M disodium hydrogen phosphate, qsp 100 mL water). The increase in the extinction at 280 nm was monitored for 2 min. It was proportional to the benzaldehyde concentration in the sample. Self-degradation of the cyanohydrin was determined in a control sample without enzyme and subtracted from the values measured for the enzyme sample. In order to determine the remaining activity in the course of the stability tests described in Example 5d, a slightly altered procedure was used: 870 µl of citrate buffer (50 mM, pH 4) was supplemented with 30 µl of enzyme sample, the reaction was started by adding 100 µl of mandelonitrile (60 mM in 50 mM of citrate buffer, pH 2) and monitored for 2 minutes at 280 nm. The advantage of this variation is that the non-enzymatic reaction is almost completely suppressed, but nevertheless the control reaction without the enzyme was monitored for each series of measurements. The enzyme activity is, however, much lower with this procedure.

Ib) Cleavage of Various Cyanohydrins, Determination of Hydrocyanic Acid (Microtitre Plate Test):

140 µl of citrate-phosphate buffer, pH 5 (see Ia) was supplemented with 10 µl of enzyme sample. As was described in Ia, a control was used in each series of measurements (self-degradation of the cyanohydrin in question in the absence of the enzyme) and subtracted from the determined values. The enzymatic reaction was started using 10 µl of substrate solution (any cyanohydrin, 300 mM in 0.1 M citric acid) and stopped after 5 min with 10 µl of 100 mM N-chlorosuccinimide (with a 10× excess (w/w) of succinimide). The liberated hydrocyanic acid reacts with N-chlorosuccinimide and the subsequently added mixture of isonictonic acid and barbituric acid (65 mM/125 mM in 0.2 M of soda lye) to form a violet colorant the formation rate of which correlated with the quantity of HCN (Andexer et al, 2006).

II) Synthesis of Cyanohydrins:

The example used for the synthesis was in this case a transformation in a two-phase system. Other possibilities such as synthesis in a purely organic solvent (also, for example with an immobilized enzyme), in aqueous systems as well as in other unconventional solvents such as ionic liquids can also be used for the synthesis of cyanohydrins. The reaction system used was a two-phase system of citrate buffer, pH 4 and diisopropyl ether in a ratio of 1:1 (total 5 mL). The reaction took place with 20 U/mL of purified lyophilized HNL at 10° C. and 400 rpm. The substrates were added in a ratio of 1:5 (50 mM aldehyde/ketone and 250 mM HCN). Depending on the reaction rate, the substrates were transformed for 1 h to several days. The samples removed were examined on a gas chromatograph after derivatization (500 µL dichloromethane, 50 µL trifluoroacetic acid anhydride, 50 µL of pyridine+50 µL sample from organic phase). To this end, the CP-3800 gas chromatograph from Varian (FID detector) was used with a CP Chirasil-DEX CB column (length 25 m, internal diameter 0.25 mm, film thickness 0.25 µm) from the same firm. The carrier gas was helium at a flow rate of 2 mL/min. The following temperature program was suitable for almost all products except for 3-phenoxybenzaldehyde cyanohydrin: the column was kept at 50° C. for 1 min then heated at a heating rate of 3°/min to 110° C.; this temperature was maintained for 15 min. For 3-phenoxybenzaldehyde cyanohydrin, the column was maintained at 110° C. for 1 min then heated to 130° C. at a heating rate of 5°/min; this temperature was maintained for 80 min.

Unexpectedly, the enzyme is (R) selective, since HNLs up to now from the α/β-hydrolase family all favour (S) enantiomers. The transformed substrates encompass both aliphatic and aromatic compounds, however aldehydes were preferably accepted over ketones.

a) Activities for the Cleavage of Cyanohydrins:

The activities were measured for the cleavage of various commercially available cyanohydrins, however the individual substrates could only be compared with each other in a very limited manner since the substrates a) were partly racemic and also partly achiral and b) the purity of the commercially available substances varied widely. Pollution of the substrates with the corresponding aldehyde or ketone can inhibit the enzyme; this effect arises, for example, in the HNL from *Manihot esculenta* which is inhibited by benzaldehyde (impurity in mandelonitrile). For these reasons, observation of the cleavage reaction acts only as an initial overview (Table 3). Results which could be used for prediction purposes were obtained by examining the synthesis of cyanohydrins with subsequent gas chromatographic analysis.

TABLE 3

Substrate spectrum of AtHNL (cleavage reaction)

| Substrate (cyanohydrin) | $R^1$ | $R^2$ | HCN-Test (see Ib above) | Benzaldehyde Test (see Ia above) |
|---|---|---|---|---|
| Acetaldehyde cyanohydrin | H | H | <0.05 | |
| Propionaldehyde cyanohydrin | H | $CH_3$ | <0.05 | |

TABLE 3-continued

Substrate spectrum of AtHNL (cleavage reaction)

| Substrate (cyanohydrin) | R¹ | R² | HCN-Test (see Ib above) Specify activity (U/mg) | Benzaldehyde Test (see Ia above) Specify activity (U/mg) |
|---|---|---|---|---|
| Benzaldehyde cyanohydrin | H | phenyl | 4.3 | 12.5 |
| 3-Phenoxybenzaldehyde cyanohydrin | H | 3-phenoxyphenyl | 0.3 | |
| Acetone cyanohydrin | CH₃ | CH₃ | <0.05 | |
| Cyclohexanone cyanohydrin | | cyclohexyl (gem) | 0.11 | | b) Activities for the Synthesis of Cyanohydrins from Aldehydes/Ketones and Hydrocyanic Acid in a Two-Phase System:

For the AtHNL, a partial substrate spectrum was recorded (Table 4). The direction of synthesis was observed; the corresponding aldehyde was supplemented with hydrocyanic acid in a two-phase system (results in Table 4). All of the tested aldehydes were transformed; for ketones, only low activities were observed.

c) Demonstration of Stereoselectivity

Figure 6:
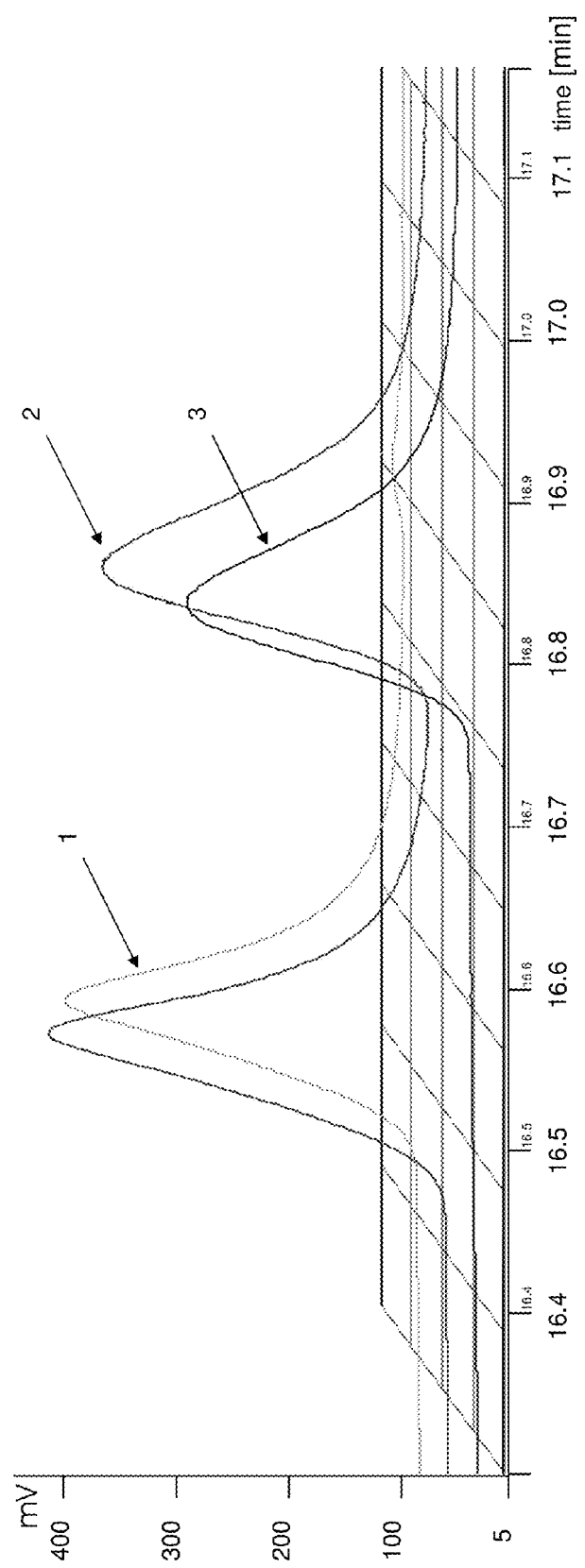
FIG. 6 is a diagram showing the stereoselectivity of the polypeptide of the invention using chiral gas chromatography: 1=product from AtHNL: (R)-mandelonitrile, 2=racemic mandelonitrile, 3=(S)-mandelonitrile; the AtHNL product on the synthesis of mandelolitrile from benzaldehyde and HCN was investigated, compared with pure (S)-mandelonitrile and racemic mandelonitrile.

The stereoselectivity was determined on the one hand using chiral gas chromatography (FIG. 6), and on the other hand in a cleavage test with enantiomerically pure benzaldehyde cyanohydrin. Only the (R) enantiomer formed or was transformed. As already described above, this circumstance was not predicted; the great similarity with MeHNL or HbHNL meant that (S) selectivity was assumed.

Example 7

Structural Investigations

Figure 7:
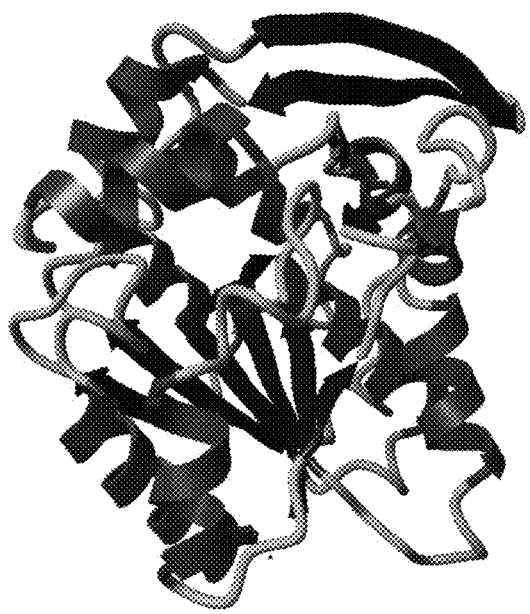
FIG. 7 is a structural model of the polypeptide of the invention based on the crystalline structure of hydroxynitrile lyase from *Hevea brasiliensis*: the model was based on the crystalline structure of the homologous HbHNL.

Based on the crystal structure of the HNL from *Hevea brasiliensis* (PDB No. 1 QJ4 (no substrate, 1 SC9 (with acetone cyanohydrin)), a structural model of AtHNL was produced. FIG. 7).

TABLE 4

Partial substrate spectrum of AtHNL (synthesis reaction)

| Substrate (aldehyde or ketone) | R¹ | R² | Reaction period (h) | Transformation (%) | ee (R) (%) |
|---|---|---|---|---|---|
| Benzaldehyde | H | phenyl | 2 | >99.9 | 95 |
| 3-phenoxybenzaldehyde | H | 3-phenoxyphenyl | 61.5 | 73 | 78 |
| 4-methoxybenzaldehyde | H | 4-methoxyphenyl (—OCH₃) | 22.5 | 22.6 | 0 |
| 4-chlorobenzaldehyde | H | 4-chlorophenyl (—Cl) | 7 | 98 | 95 |
| Phenylacetaldehyde | H | benzyl | 22.5 | 90 | 71 |

TABLE 4-continued

Partial substrate spectrum of AtHNL (synthesis reaction)

| Substrate (aldehyde or ketone) | | Reaction period (h) | Transformation (%) | ee (R) (%) |
|---|---|---|---|---|
| | $R^1$ | $R^2$ | | | |
| Hexanal | H | $C_5H_{11}$ | 2.5 | 98 | n.d. |
| Heptanal | H | $C_6H_{13}$ | 2 | >99.9 | >80% |
| Octanal | H | $C_7H15$ | 5 | 89 | n.d. |
| Benzyl acetone | $CH_3$ | (phenethyl) | 22 | 9 | 40 |
| 2-butanone | $CH_3$ | $C_2H_5$ | 22 | >95 | 0 |
| 2-pentanone | $CH_3$ | $C_3H_7$ | 22 | >95 | 0 |
| 2-hexanone | $CH_3$ | $C_4H_9$ | 22 | n.d. | 0 |
| 2-heptanone | $CH_3$ | $C_5H_{11}$ | 22 | 9 | 9 |
| 2-octanone | $CH_3$ | $C_6H_{13}$ | 22 | 0 | n.d. |

Assumption of a α/β-hydrolase fold was obvious based on the great similarity (>65%) with known α/β-hydrolase-resembling HNLs and the conserved catalytic triad (S, D, H) and was supported by the model. Sterically too, the residues of the catalytic triad are correctly positioned. Further, the model provides clues to explaining the stereoselectivity and the substrate spectrum. On observing the substrate spectrum, it appears that the tested aldehyde can be transformed very well while the activity towards ketones is rather weak. The comparison of the model structure with the structure of HbHNL (with bound acetone cyanohydrin substrate), however, leads to the conclusion that this problem can be remedied by a point mutation. By comparison with the HbHNL structure, it is clear that one amino acid side chain (asparagine 12) in the model projects a long way into the binding pocket and collides with a methyl group of the substrate, while in the HbHNL crystal structure there is a less sterically hindering amino acid (threonine) in this position.

The structural analysis of the hydroxynitrile lyase of the invention also shows that the substrate in the active centre of AtHNL is stabilized by the alanine in position 13 (A13), the phenylalanine in position 82 (F82, backbone-NH group) and the asparagine in position 12 (N12, demonstrated by exchange). Further, because of their substrate contact, the amino acids serine in position 81 (S81) and histidine in position 236 (H236) can be assigned to the active centre. (In order to complete the catalytic triad, the asparaginic acid in position 208 (D208) also belongs to it).

Further amino acid residues in the substrate range, i.e. in or in the vicinity of the catalytic centre or substrate binding pocket are as follows:

M237, A210, L158, F153, L129, M149, Y14, C132, L147, F179, A13, L119, F107 and I211.

A further substrate spectrum of the hydroxynitrile lyase of the invention can be seen in Table 5.

Initial attempts to stabilize the AtHNL at low pHs showed that sorbitol and saccharose at a pH of 5 cause a rise in the half life from 3 hours to more than 72 hours (200 mg/ml of sorbitol).

TABLE 5

Extended substrate spectrum for AtHNL

| Substrate | Time (h) | Transformation (%) | ee (R) (%) | Non-enzymatic transformation (%) (control reaction without enzyme) |
|---|---|---|---|---|
| R = H— | 1 | 2 | >99 | >99 | 14 |
| R = o-F— | 2 | 2 | >99 | 99 | 17 |
| R = o-Cl— | 3 | 2 | >99 | 99 | 26 |
| R = o-Br— | 4 | 6 | 99 | 98 | 42 |
| R = o-I— | 5 | 3 | >99 | >95 | 26 |
| R = m-F— | 6 | 2 | >99 | >99 | 22 |
| R = m-Cl— | 7 | 3 | 99 | >99 | 7 |
| R = m-Br— | 8 | 6 | 99 | 95 | 9 |
| R = m-I— | 9 | 6 | 98 | 93 | 5 |
| R = m-phenoxy | 10 | 22 | 83 | >95 | 0 |
| R = p-F— | 11 | 2 | >99 | >99 | 7 |
| R = p-Cl— | 12 | 2 | >99 | >99 | 4 |
| R = p-Br— | 13 | 3 | 99 | >99 | 4 |
| R = p-I— | 14 | 6 | 99 | 92 | 7 |
| R = p-hydroxy- | 15 | 3 | 96 | 97 | 3 |
| R = p-methoxy- | 16 | 22 | 87 | 68 | 14 |

TABLE 5-continued
Extended substrate spectrum for AtHNL
| Substrate | | Time (h) | Transformation (%) | ee (R) (%) | Non-enzymatic transformation (%) (control reaction without enzyme) |
|---|---|---|---|---|---|
| 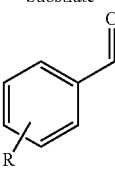 | 17 | 22 | 97 | 96 | 97 |
| 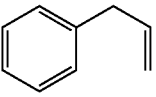 | 18 | 22 | 99 | 68 | 97 |
| 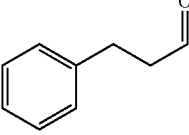 | 19 | 6 | 68 | n.d.[b] | 6 |
| 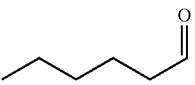 | 20 | 6 | 99 | 98 | 78 |
| 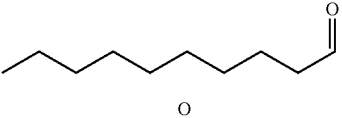 | 21 | 22 | 56 | >95 | 0 |
| 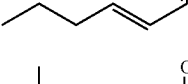 | 22 | 3 | 53 | n.d.[b] | 0 |
| 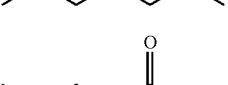 | 23 | 22 | 0 | — | 0 |
|  | 24 | 6 | 48 | 95 | 2 |
|  | 25 | 22 | 2 | — | 0 |
|  | 26 | 3 | 94 | —[c] | 76 |
| 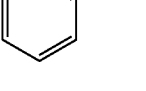 | 27 | 22 | 7 | n.d. | 0 |
| 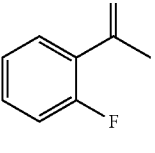 | 28 | 22 | 8 | 95 | 0 |

TABLE 5-continued

Extended substrate spectrum for AtHNL

| Substrate 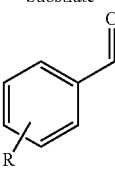 R | Time (h) | Trans- formation (%) | ee (R) (%) | Non-enzymatic trans- formation (%) (control reaction with- out enzyme) |
|---|---|---|---|---|
| 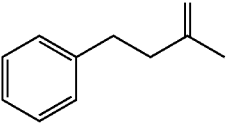 | 29 | 3 | 1 | — | 0 |

To support the structural model and improve the polypeptide of the invention and also to explain the reaction mechanism, insertion of the following point mutations into SEQ ID NO: 1 proved to be particularly advantageous:

verification of α/β-hydrolase folding: the residues identified as the catalytic triad were exchanged for other (sterically similar, but without the corresponding function) amino acids; the resulting polypeptide no longer exhibited any activity: S81A; D208N; H236F;

broadening of substrate spectrum to ketones: N12T, preferably as the double mutation with Y14C;

reversal of enantioselectivity: L129W and/or Y14C.

The substantiated attempts to improve the polypeptide of the invention (for example as regards the substrate spectrum) have meant that, in addition to the wild type protein, the invention also claims variants which were produced by introducing individual point mutations into the DNA sequence (rational design) as well as by directed evolution methods (epPCR, saturation mutagenesis, etc).

Example 8

Production of AtHNL Using Fed Batch Fermentation on a 15 L Scale

In order to produce AtHNL on a larger scale, the expressed stock can be fermented in a fed bioreactor. The method used was a standard protocol for high cell density fermentation of E. coli (Korz et al, 1995). A 42 L fermenter was inoculated with 100 ml of pre-culture in 10 L of medium; the culture was grown in the pre-defined medium for 27 h at 30° C. The feed rate depended on the quantity of glucose required to obtain optimum growth. After 27 h, induction with IPTG was started; thereafter the protein was expressed for a further 16 h, and then the cells were harvested by centrifuging. 1.75 kg of cells were obtained from a final volume of 15 L. For the subsequent purification (see Example 4), 20 g of cells were used, resuspended in solubilizing buffer, solubilized by ultrasound, centrifuged and the residue was used as the unrefined extract. This unrefined extract (final volume approx 30 ml) had a volumetric activity of approx 800 U/ml and a specific activity of 13.3 U/mg. After purification over a Q-Sepharose column and subsequent desalting (see Example 4) as well as lyophilization, an activity of 2.5 U/mg of lyophilisate and a specific activity of approximately 40 U/mg protein was obtained. Starting from 20 g of cells, approximately 6 g of lyophilisate was produced corresponding to a total activity of approximately 15 kU. A high cell density fermentation with 15 L final volume thus produced a total of 525 g of lyophilisate with a total activity of 1300 kunits.

This example shows that the polypeptide of the invention can surprisingly also be produced readily in large quantities. The yield in the fermenter corresponded to that obtained on the laboratory scale.

LITERATURE

Albrecht J, Jansen I, Kula M R (1993) Improved Purification of an (R)-Oxynitrilase from Linum-Usitatissimum (Flax) and Investigation of the Substrate Range. Biotechnol Appl Biochem 17: 191-203

Andexer J, Guterl J K, Pohl M, Eggert T (2006) A high-throughput screening assay for hydroxynitrile lyase activity: Chem Commun 40: 4201-4203

Bray E A (2002) Classification of genes differentially expressed during water-deficit stress in Arabidopsis thaliana: an analysis using microarray and differential expression data. Ann Bot 89: 803-11

Bauer M, Griengl H, Steiner W (1999) Kinetic studies on the enzyme (S)-hydroxynitrile lyase from hevea brasiliensis using initial rate methods and progress curve analysis. Biotechnol Bioeng 62: 20-29

Bühler H, Effenberger F, Förster S, Roos J, Wajant H (2003) Substrate specificity of mutants of the hydroxynitrile lyase from Manihot esculenta. Chembiochem 4:211-216

Fechter M H, Griengl H (2004) Hydroxynitrile lyases: Biological sources and application as biocatalysts. Food Technol Biotechnol 42: 287-294

Gaisberger R P, Fechter M H, Griengl H (2004) The first hydroxynitrile lyase catalysed cyano-hydrin formation in ionic liquids. Tetrahedron Asymmetry 15: 2959-2963

Glieder A, Weis R, Skranc W, Poechlauer P, Dreveny I, Majer S, Wubbolts M, Schwab H, Gruber K (2003) Comprehensive step-by-step engineering of an (R)-hydroxynitrile lyase for large-scale asymmetric synthesis. Angew Chem Int Ed Engl 42:4815-4818

Hasslacher M, Kratky C, Griengl H, Schwab H, Kohlwein S D (1997) Hydroxynitrile lyase from Hevea brasiliensis: molecular characterization and mechanism of enzyme catalysis. Proteins 27: 438-449

Korz D J, Rinas U, Hellmuth K, Sanders E A and Deckwer W-D (1995) Simple fed-batch technique for high cell density cultivation of Escherichia coli. J Biotechnol 39 (1). 59-65

Lee F, Mulligan R, Berg P, Ringold G (1981) Glucocorticoids regulate expression of dihydrofolate reductase cDNA in mouse mammary tumour virus chimaeric plasmids. Nature 294: 228-232

Ollis D L, Cheah E, Cygler M, Dijkstra B, Frolow F, Franken S M, Harel M, Remington S J, Silman I, Schrag J (1992) The alpha/beta hydrolase fold. Protein Eng 5:197-211

Rosenthaler L (1908) Durch Enzyme bewirkte asymmetrische Synthesen. Biochem Z 14:238-253

Schmidt M, Griengl H (1999) Oxynitrilases: From cyanogenesis to asymmetric synthesis. Biocatalysis—from Discovery to Application 200: 193-226

Sharma M, Sharma N N, Bhalla T C (2005) Hydroxynitrile lyases: At the interface of biology and chemistry. Enzyme Microb Technol 37:279-294

Wäspi U, Misteli B, Hasslacher M, Jandrositz A, Kohlwein S D, Schwab H, Dudler R (1998) The defense-related rice gene Pir7b encodes an alpha/beta hydrolase fold protein exhibiting esterase activity towards naphthol AS-esters. Eur J Biochem 254:32-37

The invention claimed is:

1. A method for the synthesis of chiral cyanohydrins from at least one carbonyl compound and hydrocyanic acid comprising:
providing said at least one carbonyl compound and said hydrocyanic acid and carrying out a reaction in presence of at least one isolated polypeptide that has hydroxynitrile lyase activity, wherein the polypeptide comprises
(a) the amino acid sequence according to SEQ ID NO: 1;
(b) an amino acid sequence comprising all of SEQ ID NO: 1 except for one or more amino acid replacements, wherein said replacements are selected from the group consisting of:
(i) asparagine in position 12 of SEQ ID NO: 1, replaced with threonine or alanine;
(ii) tyrosine in position 14 of SEQ ID NO: 1, replaced with cysteine or alanine;
(iii) leucine in position 129 of SEQ ID NO: 1, replaced with tryptophan; and
(iv) a combination of (i), (ii) and (iii); or
(c) an amino acid sequence which
(i) differs from SEQ ID NO: 1 solely by up to 20 amino acids which have been deleted, inserted and/or substituted or
(ii) has more than 90% sequence identity with SEQ ID NO:1, wherein the chiral cyanohydrins are synthesized.

2. The method according to claim 1, wherein the polypeptide comprises the amino acid sequence according to SEQ ID NO:1.

3. The method according to claim 1, wherein the polypeptide comprises the amino acid sequence comprising all of SEQ ID NO: 1 except for one or more amino acid replacements, wherein said replacements are selected from the group consisting of:
(i) asparagine in position 12 of SEQ ID NO: 1, replaced with threonine or alanine;
(ii) tyrosine in position 14 of SEQ ID NO: 1, replaced with cysteine or alanine;
(iii) leucine in position 129 of SEQ ID NO: 1, replaced with tryptophan; and
(iv) a combination of (i), (ii) and (iii).

4. A method for the synthesis of chiral cyanohydrins from at least one carbonyl compound and hydrocyanic acid comprising:
providing said at least one carbonyl compound and said hydrocyanic acid and carrying out a reaction in the presence of at least one polypeptide, wherein said polypeptide has hydroxynitrile lyase activity and is expressed by a cell which contains an isolated nucleic acid molecule encoding said polypeptide, wherein said isolated nucleic acid molecule comprises:
a) a nucleotide sequence encoding SEQ ID NO: 1;
b) SEQ ID NO: 2;
c) a nucleotide sequence which comprises all of SEQ ID NO: 2 except for one or more codon replacements, wherein the codon replacements are selected from the group consisting of:
  (i) codon twelve is replaced with ACC, ACT, ACA, ACG, GCT, GCC, GCA or GCG;
  (ii) codon fourteen is replaced with TGT, TGC, GCT, GCC, GCA or GCG;
  (iii) codon one hundred and twenty-nine is replaced with TGG; and
  (iv) a combination of (i), (ii) and (iii); or
d) a nucleotide sequence which has at least 90% sequence identity with SEQ ID NO: 2,
and wherein the chiral cyanohydrins are synthesized.

5. The method of claim 4, wherein the nucleic acid molecule is part of a vector.

6. The method of claim 4,
wherein the nucleotide sequence comprises:
  a) a nucleotide sequence encoding SEQ ID NO: 1;
  b) SEQ ID NO: 2; or
  c) a nucleotide sequence which has at least 90% identity with SEQ ID NO: 2.

7. The method of claim 4, wherein the nucleotide sequence comprises a nucleotide sequence that has at least 90% sequence identity with SEQ ID NO: 2.

8. The method of claim 4, wherein the nucleotide sequence comprises a nucleotide sequence that has at least 95% sequence identity with SEQ ID NO: 2.

9. The method of claim 4,
wherein the nucleotide sequence comprises SEQ ID NO: 2 or has at least 95% sequence identity with SEQ ID NO: 2.

10. The method of claim 4, wherein the nucleic acid molecule is operatively coupled with at least one regulatory sequence.

11. The method of claim 10, wherein the regulatory sequence comprises a promoter sequence and/or a transcription termination sequence and/or a regulator gene.

12. The method of claim 4, wherein the nucleic acid molecule is coupled with at least one further nucleotide sequence which codes for a further polypeptide.

13. The method according to claim 1, wherein the hydroxynitrile lyase activity is (R)-selective or wherein the polypeptide belongs to the α/β-hydrolase family.

14. The method according to claim 1, wherein the polypeptide belongs to the α/β-hydrolase family.

* * * * *